United States Patent [19]
Walen

[11] Patent Number: 6,045,564
[45] Date of Patent: Apr. 4, 2000

[54] MULTI-PURPOSE SURGICAL TOOL SYSTEM

[75] Inventor: James G. Walen, Kalamazoo, Mich.

[73] Assignee: Stryker Corporation, Kalamazoo, Mich.

[21] Appl. No.: 08/970,603

[22] Filed: Nov. 14, 1997

Related U.S. Application Data

[62] Division of application No. 08/885,591, Jul. 1, 1997, which is a division of application No. 08/693,395, Aug. 2, 1996.

[51] Int. Cl.⁷ .................................................. A61B 17/00
[52] U.S. Cl. ................................................ 606/167; 606/1
[58] Field of Search ..................... 606/167–171, 606/79, 80, 185, 180; 279/131; 30/166.3; 433/128

[56] References Cited

U.S. PATENT DOCUMENTS

| Re. 27,032 | 1/1971 | Hall . |
|---|---|---|
| 3,827,149 | 8/1974 | Brennan . |
| 3,835,858 | 9/1974 | Hagen . |
| 4,310,310 | 1/1982 | Bailey . |
| 4,515,564 | 5/1985 | Löhn . |
| 5,222,956 | 6/1993 | Waldron . |
| 5,265,343 | 11/1993 | Pascaloff . |
| 5,421,682 | 6/1995 | Obermeier et al. . |
| 5,505,737 | 4/1996 | Gosselin et al. . |
| 5,522,829 | 6/1996 | Michalos . |
| 5,542,846 | 8/1996 | Quinn et al. ............................ 433/128 |
| 5,569,282 | 10/1996 | Werner . |
| 5,571,137 | 11/1996 | Marlow et al. . |
| 5,697,158 | 12/1997 | Klinzing et al. ........................ 30/166.3 |

FOREIGN PATENT DOCUMENTS

| 0 670 149 A1 | 9/1995 | European Pat. Off. . |
|---|---|---|
| 686 113 | 1/1996 | Switzerland . |
| WO 96/10962 | 4/1996 | WIPO . |

OTHER PUBLICATIONS

The Hall Ultra Power Surgical Drill System Instruction Manual, Title page, pp. 26–29, 1996.
The Med$^{next}$ High Speed, High Power Bone Dissecting System, 2 pages, 1996.
Zeppelin Motordrill System Operating Procedures, 4 pages, 1996.
PCT Examination Report for Application No. PCT/US97/14491, Sep., 1998.
Anspach, Black Max Universal Instrument System, 1995, (4 pages).

*Primary Examiner*—Michael Buiz
*Assistant Examiner*—Vikki Trinh
*Attorney, Agent, or Firm*—Flynn, Thiel, Boutell & Tanis, P.C.

[57] ABSTRACT

A surgical tool system (20) with replaceable surgical cutting accessories (26) and attachments (34) for holding the tools. This system includes a handpiece (22) to which the cutting accessory and attachment are releasably attached. Collet (50) located inside a drill housing (44) located at one end of the handpiece securely fastens the surgical tool to a motor (24) also located in the handpiece. Leaf spring assembly (46) flush with the drill housing releasably secures the attachment in place. A single actuating collar (52) located around the outside of the drill housing both controls the locking force supplied by the collet and selectively relaxes the leaf spring assembly.

15 Claims, 16 Drawing Sheets

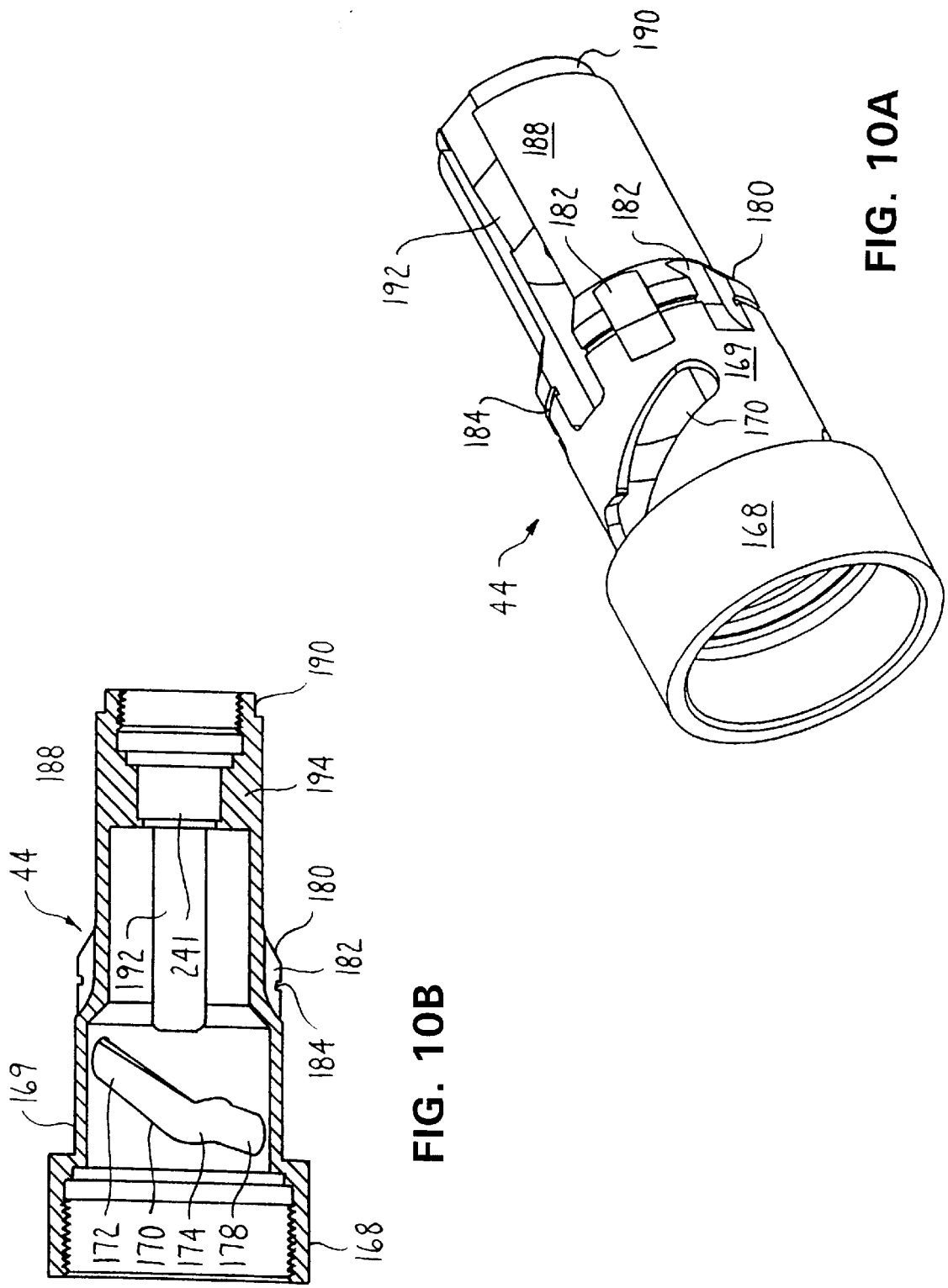

MULTI-PURPOSE SURGICAL TOOL SYSTEM

This application is a divisional of application Ser. No. 08/885,591 filed Jul. 1, 1997 which is a divisional of application Ser. No. 08/693,595 filed Aug. 2, 1996.

FIELD OF THE INVENTION

This invention relates generally to a surgical tool system and, more particularly, to a surgical tool system with a number of readily interchangeable components.

BACKGROUND OF THE INVENTION

In modern surgery one of the most important instruments available to medical personnel is the powered surgical tool. Typically this tool comprises some type of handpiece in which a motor is housed. Secured to the handpiece is a cutting accessory designed to be applied to a surgical site on a patient in order to accomplish a specific medical task. For example, some powered surgical tools are provided with drills or burrs for cutting bores into a hard tissue or for selectively removing the hard tissue. Still other powered surgical tools are provided with saw blades as the cutting accessories. These tools are used for separating large sections of hard and soft tissue. The ability to use powered surgical tools on a patient has lessened the physical strain of physicians and other personnel when performing medical procedures on a patient. Moreover, most surgical procedures can be performed more quickly and more accurately with powered surgical tools than with the manual equivalents that proceeded them.

While powered surgical tools have provided to be both an aid to patients and medical personnel, they are not without some disadvantages. A problem with some surgical tools is that the handpiece and associated instrument are assembled as a single, permanently attached unit. Consequently, if for a particular medical procedure, it is necessary to first drill a bore in a bone and then to cut an elongated slot through the bone, it may be necessary for the doctor to be provided with two tools, each with its own cutting accessory. Furthermore, for some tasks during the procedure the physician may want to use a tool with a head that is substantially axially aligned with the handpiece. For other tasks during the same procedure the physician may want to use a tool with a head that is angled relative to the handpiece. An advantage of using these tools is that they do not block the field of view around the surgical site as much as tools with in-line heads.

There have been attempts to provide powered surgical tool systems which allow for some interchangeability of the instruments with which the tool is used. Typically, these systems include a single handpiece that has a coupling assembly to which a number of different surgical cutting accessories can be attached. These systems allow the doctor working on the patient to switch the cutting accessory being used with the handpiece as the surgical procedure progresses. An advantage of these systems is that they significantly reduce the number of handpieces that need to be provided in a surgical setting.

There have been recent attempts to enhance the utility of handpieces by providing complementary attachments. An attachment serves as the head of the handpiece to which the cutting accessory is attached. Some attachments are provided with some types of linkages that transfer the motive power from the motor internal to the handpiece to the cutting accessory. For example, some attachments are designed to provide an extended length to the handpiece. Still other attachments function as bent-angle units. These attachments direct the associated cutting accessory at an angle away from the axis of the handpiece so as to provide the surgeon with an alternative view of the surgical site. Still other attachments transfer the rotor motion of the motor internal to the handpiece into either a reciprocating or oscillatory motion. These attachments make it possible to attach saw blades to handpieces that are normally used with rotating cutting accessories. The development of attachments has further expanded the utility of basic surgical handpieces.

While current multi-tool surgical tool systems have proved useful for reducing the number of tools needed when working on an individual patient, they are not without some disadvantages. Many current surgical tool systems are designed so that the individual elements forming a tool, the handpiece and the complementary accessory, must be threadingly coupled to each other. In some of these systems, in order to ensure a positive coupling, medical personnel are required to take a wrench to the tool in order to provide the torque required to first couple the elements, and then, at a latter time to uncouple them.

Moreover, if the handpiece is provided with an attachment in addition to a cutting accessory, at a minimum the medical personnel must take time to determine which component, the cutting accessory or the attachment, they are to remove from the handpiece. Moreover, if both the cutting accessory and the attachment are to be replaced, time must be spent releasing and restoring the lock mechanisms that hold both these members to the handpiece. At a minimum, the time medical personal spend performing these coupling and uncoupling tasks only increases the time it takes to perform the surgical procedure. However, the time needed to perform these tasks lengths the time it takes to perform the surgical procedure. Consequently, this lengthens the time the surgical site is open and exposed to infection as well as the time patient is exposed to anesthesia. Moreover, there are instances where the time medical personnel have to spend attending to the tool and not to the patient can potentially adversely affect the well being of the patient.

Moreover, in order for these interchangeable power tools to be properly designed, they should ideally be provided with some type of lock out mechanism to prevent tool operation in the event the instrument is not fully coupled in place.

SUMMARY OF THE INVENTION

This invention relates to an improved multi-use powered surgical tool system that enables the medical personnel to easily and quickly couple different surgical cutting accessories and attachments to a single handpiece. Still another feature of the surgical tool system of this invention is that it automatically inhibits operation of the tool in the event the accessory is not properly coupled to the handpiece.

BRIEF DESCRIPTION OF THE DRAWINGS

This invention is pointed out with particularity in the claims. The above and further features of this invention may be better understood by reference to the following description taken in conjunction with the accompanying drawings, in which:

FIGS. 10A and 10B are, respectively, detailed side and cross sectional views of the rear drill housing;

DETAILED DESCRIPTION

Figure 1:
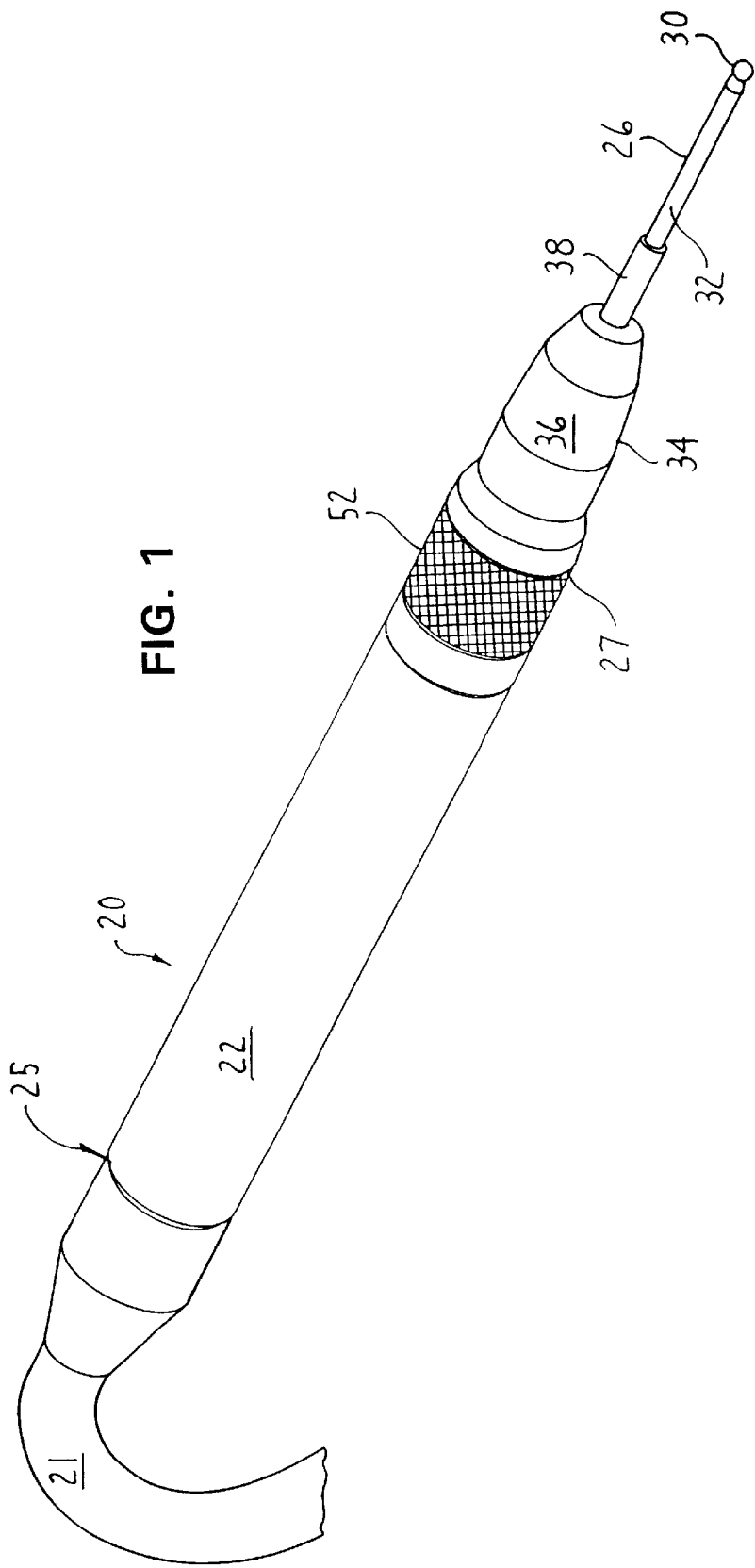
FIG. 1 is a plan view of the basic components of the surgical tool system of this invention wherein the components are assembled to form a tool.
Figure 2:
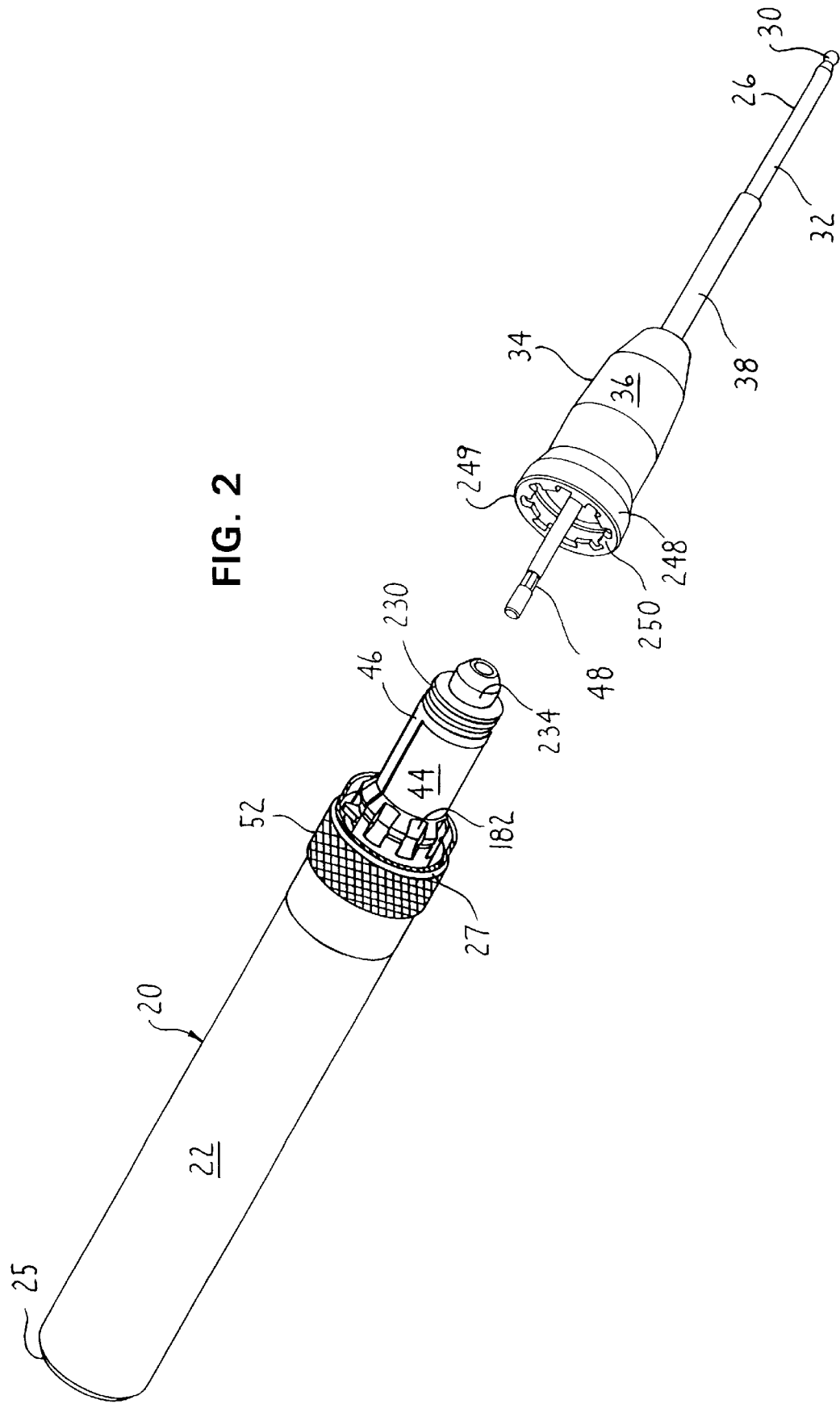
FIG. 2 is a plan view of the components of FIG. 1 illustrating the components partially decoupled from each other.
Figure 3:
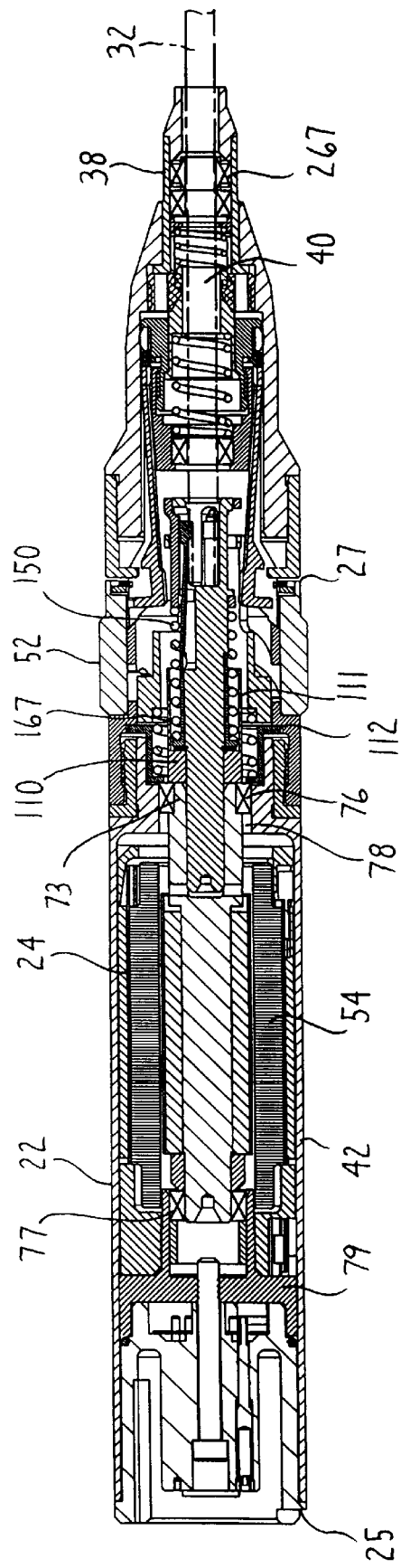
FIG. 3 is a cross sectional view of the components of FIG. 1 illustrating the components in the assembled, tool run, state.

FIGS. 1–3 illustrate the basic components of a surgical tool system 20 of this invention. System 20 includes a handpiece 22 in which a motor 24 is housed. The motor 24 is energized by power supplied to the handpiece 22 by a cable 21 releasably coupled to the bottom or base end 25 of the handpiece. A surgical cutting accessory 26 is coupled to a head end 27 of the handpiece 22, the end opposite the base end 25, to rotate in unison with the motor 24. The depicted cutting accessory 26 is a burr with a spherical head 30 formed with cutting surfaces designed to facilitate the removal of hard tissue. The cutting accessory 26 further includes an elongated, cylindrical shaft 32, to which the head 30 is attached. The shaft 32 is the actual member of the cutting accessory 26 that is coupled to the motor 24.

Surgical tool system 20 further includes an attachment 34 which is also coupled to the head end 27 of the handpiece 22. Attachment 34 includes an attachment housing 36. The attachment housing 36 is the member of the attachment 34 that is physically coupled to the handpiece 22. An attachment sleeve 38 is fixedly coupled to the narrow diameter head end of the attachment housing 36. As will be described hereinafter, attachment housing 36 and attachment sleeve 38 are formed with a bore 40. Bore 40 is occupied by the shaft 32 of the cutting accessory 26 which extends through the attachment 34. When the surgical tool system 20 is in use, the accessory shaft 32 will bear against attachment bearings 267 in sleeve 38 as a result of loads imposed on the cutting accessory 26. The attachment 34 thus provides the physical support for the cutting accessory 26 so as to prevent the accessory shaft 32 from bending when exposed to significant loads.

Figure 4:
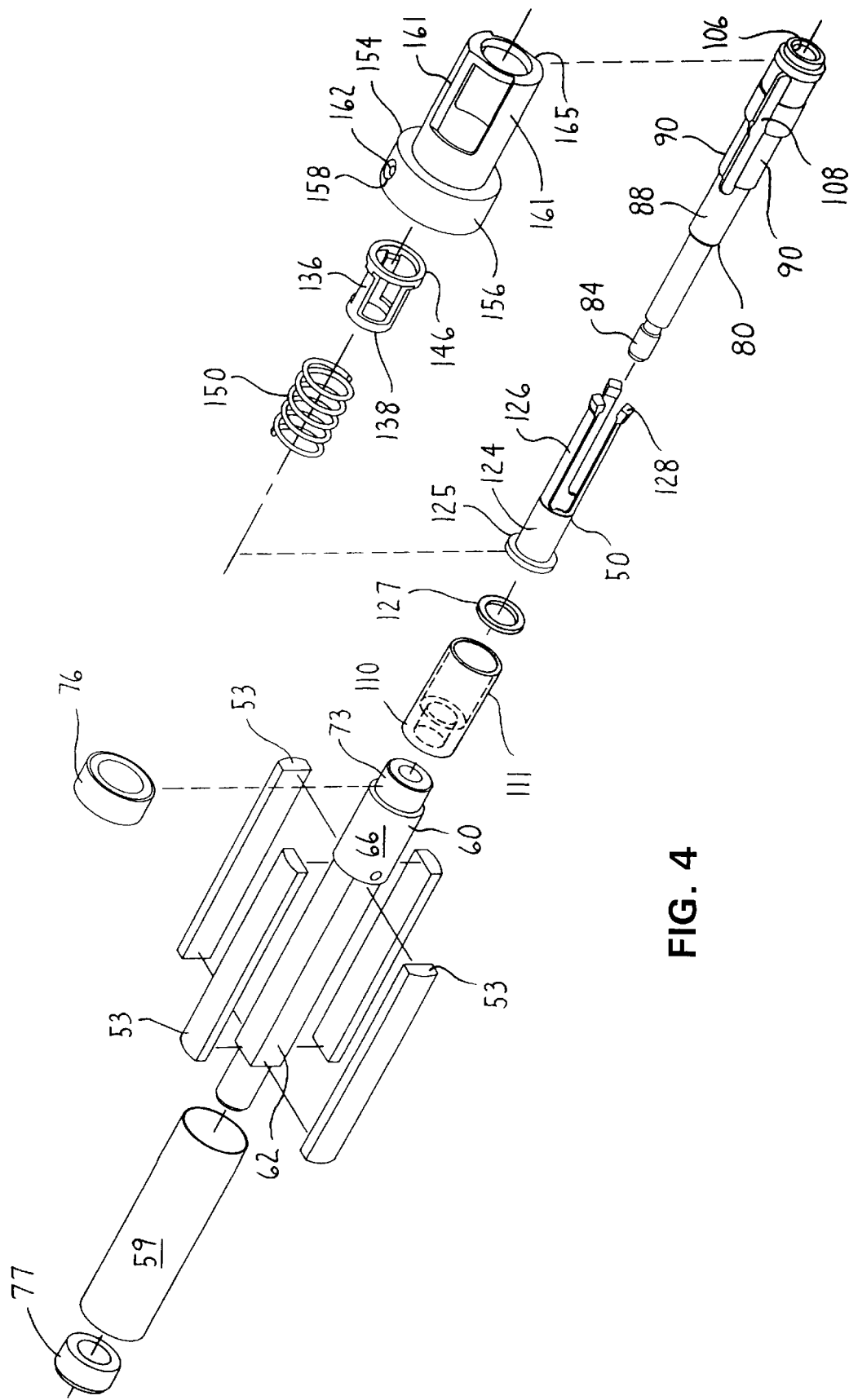
FIG. 4 is an exploded view of the interior located components that form the coupling assembly of the handpiece.

Handpiece 22 has a sleeve-like outer shell 42 in which the motor 24 and other components of the handpiece are housed. A rear drill housing 44, is fitted over the front end of the shell 42 so as to extend forwardly therefrom. (Hereinafter "forwardly" shall be understood to be along the vector extending from the base end 25 to the head end 27 of the handpiece 22.) Rear drill housing 44 has a diameter less than that of the shell 42 so as to facilitate the seating of the attachment 34 over the rear drill housing 44. A leaf spring assembly 46 seated in the rear drill housing 44 releasably secures the attachment housing 36 to the handpiece 22. The shaft 32 of the cutting accessory 26 with which the handpiece 22 is used is provided with a reduced diameter locking section 48 adjacent the butt end thereof. As will be described hereinafter, locking section 48 facilitates the securement of the cutting accessory to the handpiece motor 24 by a collet 50 (FIG. 4). An actuating collar 52 fitted over the rear drill housing 44 controls both the loading and unloading of the cutting accessory 26 to and from the handpiece 22 and the securing and release of the attachment 34 to and from the handpiece.

Figure 6A:
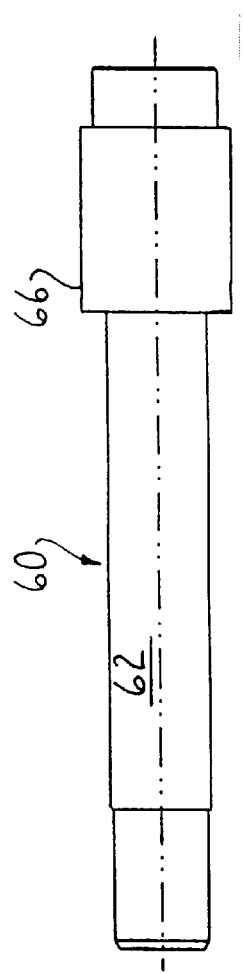
FIGS. 6A and 6B are, respectively, perspective and cross sectional views of the rotor shaft.
Figure 6B:
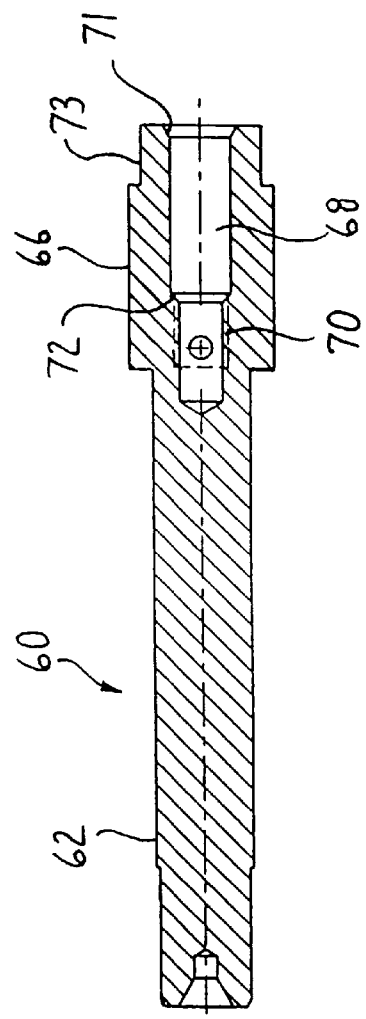

The system motor 24, now described by reference to FIGS. 3 and 4, includes a sleeve-like set of windings 54 mounted inside the handpiece shell 42 so as to be disposed against the inside wall of the shell. Motor 24 also includes a rotor shaft 60, illustrated by FIGS. 6A and 6B, that extends outwardly from the center of the windings 54. The shaft 60, includes an elongated stem 62 seated in the base of the outer shell 42. A set of magnets 53 are attached to the shaft stem 62 to provide the requisite magnetization needed to cause the rotor shaft 60 to turn. An open ended sleeve 59 is fitted around the magnets 53. In preferred versions of the invention, motor 24 is a brushless, Hallless DC motor with three distinct windings which are selectively energized in order to cause the rotation of the magnets 53 and rotor shaft 60.

Integral with the shaft stem 62 is a shaft head 66 that has a diameter larger than that of the stem. The shaft head 66 is formed to define a multi-section bore having an outer bore 68 with a large diameter and an inner bore 70 with a smaller diameter. Threading, (not illustrated) is provided around the outside of inner diameter bore 70 for a purpose described hereinafter. A first, inwardly tapered counter bore 71 is located between the end of the shaft and large diameter bore section 68. A second inwardly tapered counter bore 72 is located between bore sections 68 and 70.

The shaft head 66 is furthered formed so that the forward end thereof has a inwardly stepped surface 73 that has a diameter less than that of the rest of the head. As can best be seen by reference to FIG. 3, the front end of rotor shaft 60 is rotatably coupled to the housing shell 42 by a bearing assembly 76 that is fitted over stepped surface 73. The outer race of the bearing assembly 76 is loosely fitted around the inside wall of a portion of the housing shell that defines a neck bore 78. The rear end of the rotor shaft is coupled to the housing shell 42 by a second bearing assembly 77. Bearing assembly 77 is seated in a rear bearing housing 79 that is fitted in the rear end 25 of the outer shell.

Figure 7:
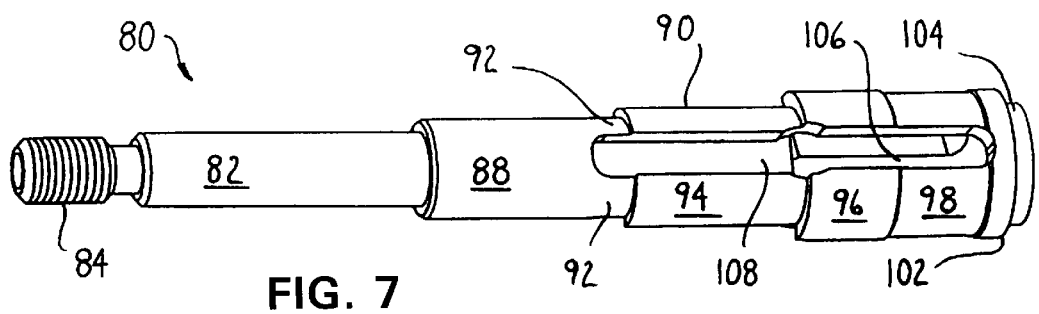
FIG. 7 is a detailed view of the collet housing.

A collet housing 80 is coupled to the rotor shaft 60 so as to turn in unison with the shaft, as is depicted by FIGS. 4 and 7. The collet housing 80, is formed out of a single piece of metal and is shaped to form an elongated, cylindrical stem 82. Collet housing stem 82 is located partially in and extends partially out of rotor shaft head outer bore 68. A threaded mounting stud 84 extends axially rearwardly from the end of the collet housing stem 82. Mounting stud 84 is threadedly coupled into rotor shaft head inner bore 70 so as to secure collet housing 80 to rotor shaft 60. In still other versions of the invention, mounting stud 84 may be press fitted into a bore of the rotor shaft 60.

Collet housing 80 further includes a solid, main body 88 formed integrally with the forward end of stem 82 that extends away from rotor shaft 60. The main body 88 has a diameter greater than that of stem 82. Three spaced-apart arms 90 extend outwardly from the outer perimeter of the collet housing main body section along axes that are parallel to the center axis of the collet housing 80. Each arm 90 includes a base section 92 with an outer diameter equal to that of the adjacent main body 88. Extending from the base section 92 each arm 90 has a first, second and third segments 94, 96, and 98, respectively. The arm first segments 94 collectively inscribe a diameter greater than that of the main body 88. The arm second segments 96 collectively inscribe a diameter greater than that inscribed by the first segments 94. The arm third segments 98 collectively inscribe a diameter between that inscribed by the first segments 94 and the second segments 96. A head ring 102 is integrally formed with the arms 90 around the outer ends of the arm third segments 98. The head ring 102 is shaped to have an outer diameter greater than that of the adjacent arm third segments 98. A small pilot ring 104 having a diameter less than that of the head ring 102 is located over the end of the head ring. Collectively, the inside surfaces of the arms 90 define a stem receiving space 106 in which the end of the shaft 32 associated with the cutting accessory 26 is seated. The interstitial separations between the housing arms 90 around the outside of the housing 80 form collet slots 108.

A balancing sleeve 110 is fitted over the portion of the collet housing stem 82 located between the rotor shaft 60 and the collet housing main section 88. When the handpiece 22 is in the final stages of assembly, the motor 24 is tested to ensure that the rotor shaft 60 and the components attached to it are properly balanced. If balancing of the rotor shaft 60 is required, outer layers of the balancing sleeve 110 can be selectively removed. Sleeve 110 is further formed to have a relatively thin walled tubular extension 111 that extends forward from the outer perimeter of the sleeve.

Figure 15A:
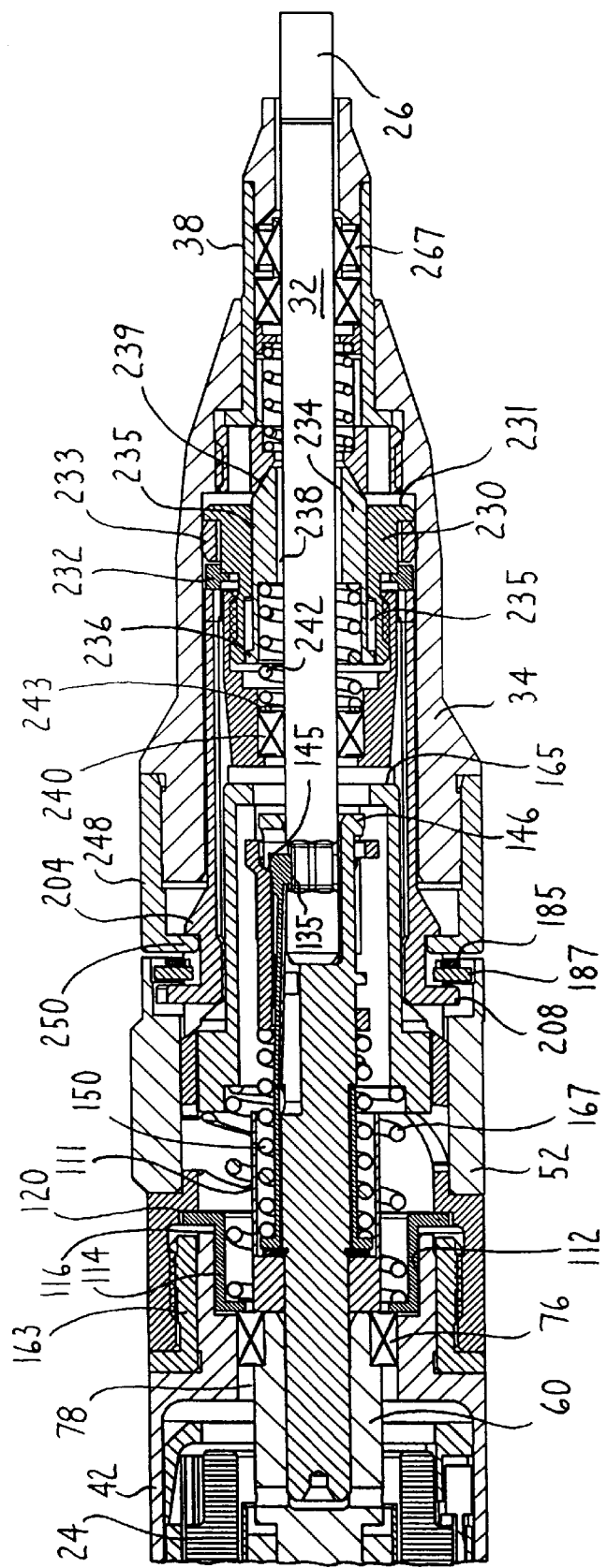
FIGS. 15A, 15B and 15C are cross sectional views of the surgical tool system of this invention when, respectively, the handpiece is in the run state, the cutting accessory load state, and the attachment release state.

A cap 112 is fitted over the exposed portion of the collet housing stem 82, best seen in FIG. 15A. Cap 112 has a sleeve-shaped body 114 that is loosely fitted into a head bore 116 at the forward end of the handpiece shell 42. Head bore 116 has a diameter greater than that of the adjoining neck bore 78. The end of cap 112 fitted into head bore 116 has an inwardly directed annular lip 118 that abuts the adjacent bearing assembly 76. The outer end of cap 112 has an outwardly directed annular lip 120.

Figure 8B:
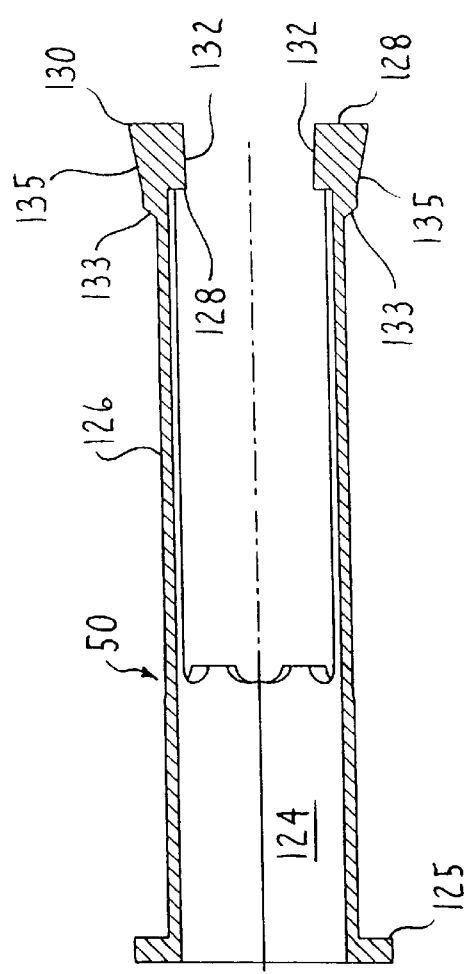
FIGS. 8A and 8B are, respectively, detailed and cross sectional views of the collet.
Figure 8A:
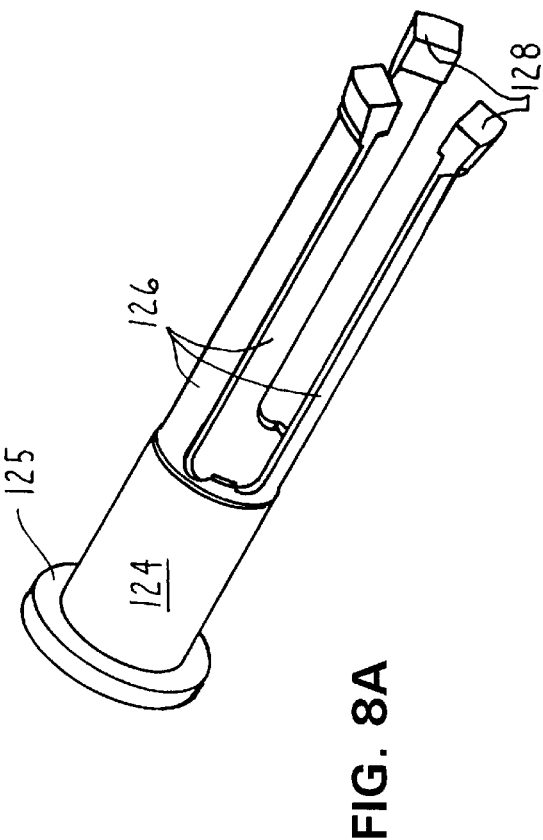

The collet 50 is now described with reference to FIGS. 4, 8A and 8B. The collet 50 is formed out a single piece of flexible metal such as stainless steel. The collet 50 is shaped to have a sleeve like main body 124 that is fitted over the collet housing main section 88. An outwardly extend annular lip 125 extends around the end of the collet main body. The rear portion of the collet main body 124 is seated inside the tubular extension 111 of sleeve 110. A thrust washer 127 is positioned inside tubular extension 110 so as to be located between the inwardly stepped surface of the sleeve 110 and the rearwardly facing surface of the lip 125 of the collet 50.

Three equidistantly spaced legs 126 extend forward of the collet main body 124. Each leg 126 is seated in a separate one of the collet slots 108 so as to be located around the outside of the stem receiving space 106 defined within the collet housing 80. A foot 128 is attached to the end of the each collet leg 126. Each foot 128 has a heal 130 that extends outwardly from the adjoining collet leg 126. More specifically, each heal is formed with a fist outwardly tapered surface 133 adjacent the surface of the collet leg from which the heal extends. Each heal further has a second tapered surface 135, with a outwardly directed taper that is less than that of the first tapered surface, that extends from the end of the first tapered surface to the end of the collet 50. Each collet foot 128 further includes a clamping toe 132 opposite the heal that is positioned to extend inwardly of the associated leg 126 and into the adjacent stem receiving space 106.

Figure 9:
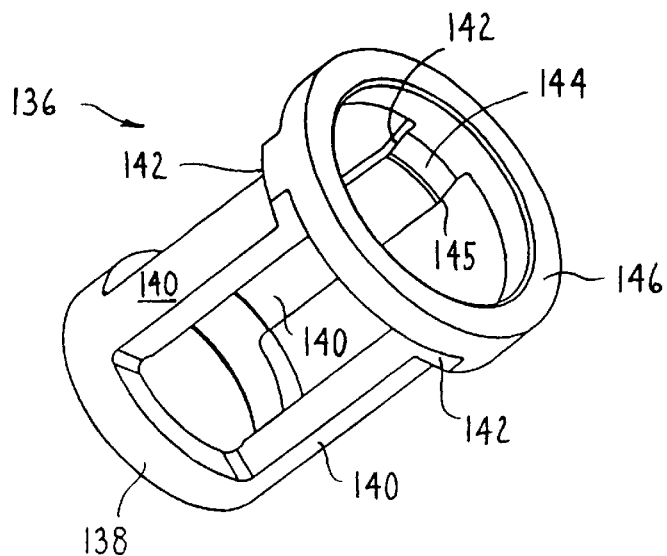
FIG. 9 is a detailed view of the collet ring.

The collet feet 128 are latched in the stem receiving space 106 by a collet ring 136, seen in FIGS. 4 and 9, that is fitted over the upper end of the collet 50. Collet ring 136 has a first, ring shaped lower web 138 which is located around the collet legs 126 immediately above the collet main body 124. Three legs 140 extend forward of the lower web 138 and are positioned to extend over the collet legs 126. Each collet housing leg 140 has an outwardly extending foot 142. Each collet housing foot 142 has an inside surface 144 that extends outwardly relative to the center of the collet ring 136. The inner surface 144 of a collect foot and the adjacent inner surface of the associated leg define an edge 145. These edge surfaces 145 are positioned to abut the adjacent second edge surfaces 135 of the collet feet 128. A ring shaped upper web 146 extend over the ends of the collet housing feet 142. Upper web 146 is shaped to have an inner surface that fits concentrically around housing head ring 102.

Collet ring 136 is normally urged upwardly by a spring 150 fitted around the collet main body 124. A rear end of spring 150 bears against collet lip 125. This end of the spring is fitted in the tubular extension 111 of bearing sleeve 110. When rotor 60 is actuated, spring 150 engages in a like rotation. Since the rear end of spring 150 is disposed within sleeve 111, outward vibration of the spring is blocked by the sleeve. The opposed end of the spring 150 bears against the base surface of the collet ring lower web 138. Since the end of the spring 150 that bears against collet lip 125 is held in position, the opposed end of the spring urges the collet ring 136 upwardly. Thus, the collet ring 136 is normally positioned so that the ring edges 145 bear against the collet feet surfaces 135 so as to lock the feet 128 into the collet housing stem receiving space 106. The forward movement on the collet ring 136 is stopped by the action of the top surface of the lower web 138 bearing against the annular stepped surface located between the collet housing arms first and second sections 94 and 96, respectively.

A collet actuator 154 selectively displaces the position of the collet ring 136 along the length of the collet housing 80 so as to release the clamping force established by the collet 50. The collet actuator 154, now described in detail by reference to FIGS. 4 and 5, includes a relatively large diameter ring shaped base 156 that is disposed about spring 150. The outer surface of the collet actuator base 156 is formed to define two, diametrically opposed seating spaces 158. Spaces 158 are each shaped to have a conical profile to facilitate the partial placement of separate ball bearings 160 therein. In the depicted version of the invention, bores 162 are shown at the base of each notch 158. Bores 162 are pilot holes that facilitate the machining of the seating spaces 158 in the collet actuator 154. The inner wall of the collet actuator base 156 is formed with an inwardly oriented flange 157 adjacent to the forward end of the actuator 156.

An intermediate ring 159 extends upwardly from the inner perimeter of flange 157. Two diametrically opposed legs 161 extend upwardly from the intermediate ring 159. Legs 161 extend along the outside of the collet ring 136. A ring-shaped end web 165 is attached to the end of the collet actuator legs 161. The legs 161 are dimensioned so that collet actuator web 165 is located above the collet ring upper web 146. The collet actuator web 165 is dimensioned so that the web 165 can be pressed against the collet ring upper web 146.

A spring 167, best seen in FIG. 15A, extends between the body 114 of cap 112 and the undersurface of the base 156 of the collet actuator 154. Spring 167 biases the collet actuator 154 forwardly so as to prevent the actuator for inadvertently releasing the locking force the collet 50 imposes of the shaft 32 of the cutting accessory 26.

Figure 5:
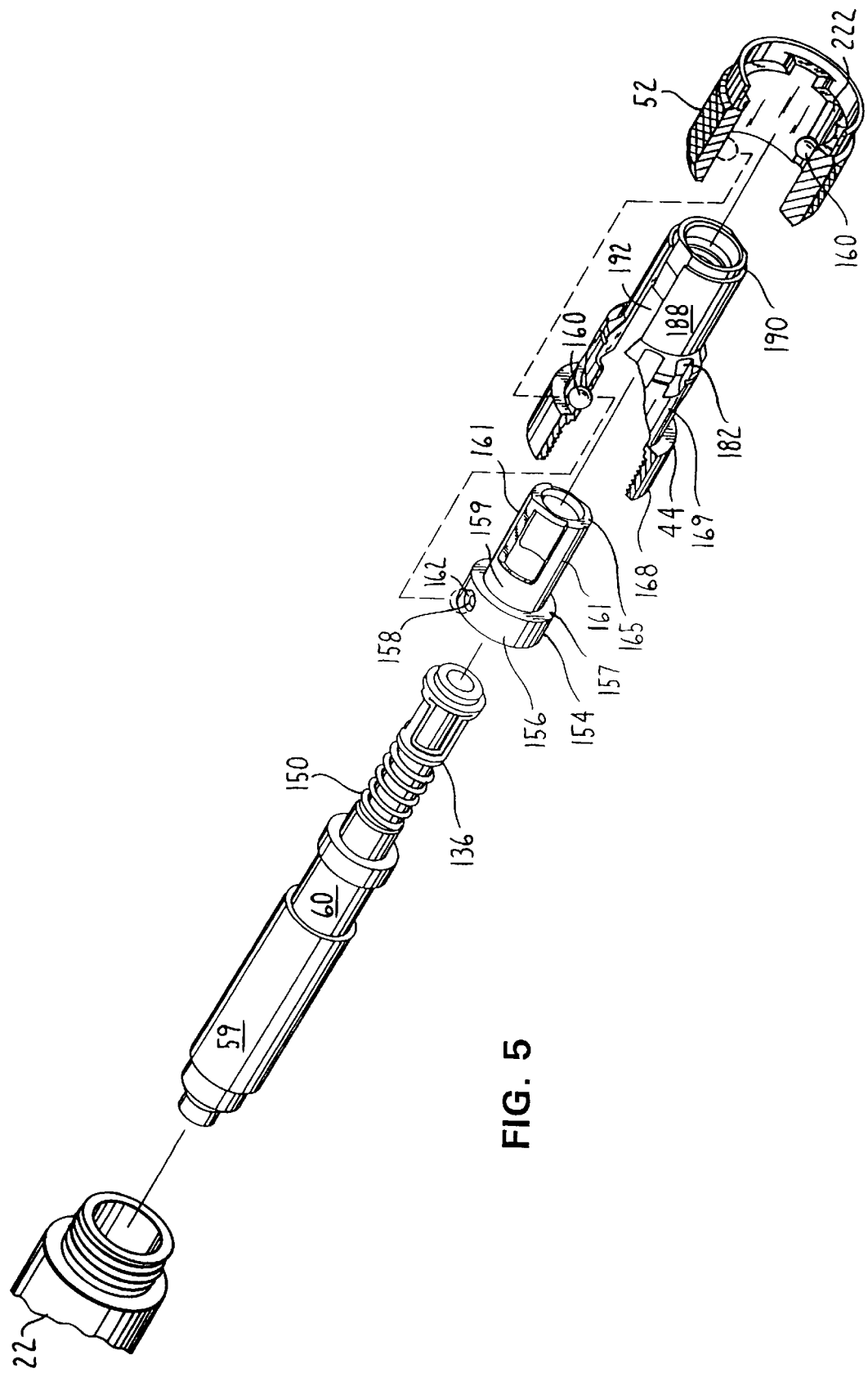
FIG. 5 is an exploded view of the outer located components that form the coupling assembly.

Collet actuator 154 is slidably fitted inside the rear drill housing 44 now described with reference to FIGS. 5, 10A and 10B. Rear drill housing 44 includes a base section 168 that has an outer diameter equal to the outer diameter of the adjacent handpiece shell 42. The rear drill housing base section 168 is securely fitted to the outer shell 42 of the handpiece 22 by an adapter ring 163 best seen by reference to FIG. 15A. Adapter ring 163 has a generally sleeve-like shape. Adapter ring is compression secured around the reduced diameter front end of the outer shell 42. The inner wall of the base section 168 of the rear drill housing 44 and the outside of the adapter ring 163 are provided with threading to facilitate the coupling of the handpiece to the adapter ring.

Immediately above rear drill housing base section 168 is a intermediate section 169 that has diameter less than that of the base section. Rear drill housing intermediate section 169 is formed to define two diametrically opposed slots 170 that extend through rear drill housing 44. Each ball bearing 160 travels in one of the slots to cause the displacement of the collet actuator 154 and the unlocking of the collet 50. Each slot 170 is formed with a first, main section 172 that extends helical downwardly from a point below the top of the housing intermediate section 169. Contiguous with each slot main section 172 is a detent 174. Relative to the adjoining main sections 172, the detents 174 extend upwardly a small distance upwardly so as to function as a ball stop space in which the ball bearing 160 can be seated. Each slot 170 is further formed with an release section 178 that extends helical downwardly a small distance from the detent 174.

Contiguous with the top of the rear drill housing intermediate section 169 is a inwardly tapered transition ring 180. The transition ring 180 and adjacent portion of the rear drill housing intermediate section 169 are shaped to define a set of slots 182 that are distributed around the outer circumference of the rear drill housing 44. As will be discussed hereinafter, slots 182 are dimensioned to receive inwardly directed teeth integral with the attachment housing 36. An annular groove 184 is formed in the rear drill housing intermediate section 168 to facilitate the attachment of a retaining ring 185 (FIG. 15B) the purpose of which will be described hereinafter.

A constant diameter stem section 188 extends upwardly from the end of rear drill housing tapered transition ring 180. The open end of the rear drill housing stem section 188 is formed to have an annular, inwardly stepped surface 190. Rear drill housing 44 is formed with two diametrically opposed, elongated leaf spring slots 192. Each leaf spring slot 192 extends from the base of the stem section stepped surface 190, through the stem section 188 and through the transition ring 180. Each leaf spring slot 192 then terminates in the intermediate section 169 immediately below the level at which the adjacent rear drill housing slots 182 terminate. Leaf spring slots 192 are shaped so as to have a relatively shallow depth adjacent the top of the drill housing stem section 188. In this section of the rear drill housing 44 there is a head 194 within the forward end of stem 188. Rearward from head 194, each leaf spring slot 192 extends through the rear drill housing 44 directly into the void space within the center of the stem 188.

The leaf spring assembly 46 is fitted over rear drill housing 44 so as to be substantially flush with the outer surface of the rear drill housing. The leaf spring assembly 46, now described with reference to FIGS. 5 and 11, includes a head 198 that is generally cylindrically shaped. The head 198 of the leaf spring is seated around the top of the drill housing stem section 188 in the space defined by the inwardly stepped surface 190. Extending downwardly from the head 198 and seated in the lead spring slots 192 are two leaf spring legs 202. Each leaf spring leg 202 is formed with an outwardly extending locking tab 204 located adjacent the drill housing transition ring 180. The tabs 204 are formed with top surfaces 206 that are dimensioned to be flush with the outer surfaces of the adjacent transition ring 180. Each locking tab 204 is further formed with a bottom surface 207 that extends perpendicularly outward from the leaf spring leg 202. The locking tab bottom surfaces 207 are the surfaces of the leaf spring 46 against which the attachment housing 36 actually abuts.

An outwardly extending foot 208 is integrally attached at the bottom of each leaf spring leg 202 so as to be spaced below the associated lock tab 204. Each foot 208 is formed with an outer surface 210 that extends diagonally outwardly away from the associated leg 202. The leaf spring legs are further formed to have heals 212 that extend from immediately below the locking tab 204 to immediately above the base of the associated foot 208. Heals 212 provide structural rigidity to the lower portion of each leaf spring leg 202. Also, as discussed hereinafter, heals 212 cooperate with collet actuator 154 to prevent unintentional inward movement of the legs 202 of the leaf spring 46.

Figure 11:
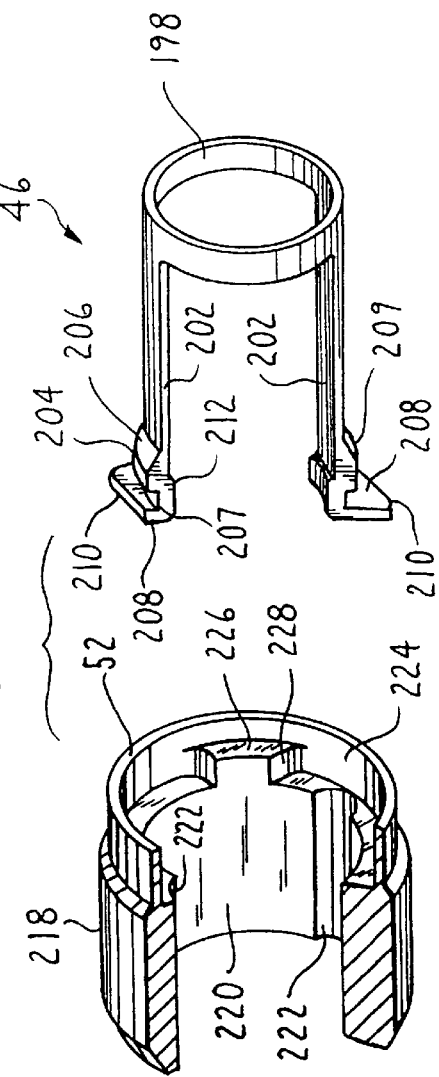
FIG. 11 illustrates the relationship of the actuating collar to the leaf spring.

The cylindrical actuating collar 52, now described with reference to FIGS. 5 and 11, both controls the loading of the cutting accessory 26 and the release of the attachment 34. The actuating collar 52 is generally sleeve-like in shape and is rotatably fitted around the drill housing intermediate section 169. Retaining ring 185 (FIG. 15B) which is snap fitted in groove 184 formed in the rear drill housing 44, holds the actuating collar 52 in position. In the depicted version of the invention, retaining ring 185 is backed up by a washer 187.

The actuating collar 52 has an outer surface 218 formed with raised bumps to facilitate manual rotation of the collar. Actuating collar 52 is further shaped to have a generally cylindrical, constant diameter inner wall 220 that extends substantially the entire length of the collar. Inner wall 220 is formed to define two diametrically opposed ball grooves 222 each of which extend the along the length of the inner wall. The ball grooves 222 are dimensioned to each receive one of the ball bearings 160.

The interior of actuating collar 52 is further shaped to have an annular, outwardly stepped surface 224 that is located around the top of the collar adjacent the inner wall 220. Stepped surface 224 is dimensioned to have a diameter greater than that of the adjacent inner wall 220. The leaf spring feet 208 are seated in the space in the actuating collar 52 defined by the top of the inner wall 220 and the adjacent stepped surface 224. A pair of diametrically opposed tabs 226, integrally formed with actuating collar 52 extend inwardly from collar stepped surface 224 towards the center axis of the collar 52. Each tab 226 is formed with a surface 228 that extends diagonally away from the adjacent stepped surface 224. As will be discussed hereinafter, when actuating collar 52 is rotated, each tab surface 228 is forced against one of the outer surfaces 210 integral with the leaf spring feet 208.

Referring to FIG. 15A, it can be seen that a nut-like front drill housing 230 is secured to the open top end of the stem section 188 of the rear drill housing 44. Front drill housing 230 has a outwardly directed circumferential flange 231. A spacer ring 232 and drag ring 233 are fitted around the outside of the front drill housing so as to be located between the top of the head 198 of the leaf spring assembly 46 and the rear surface of front drill housing flange 231. Spacer ring 232 is pressed against the head 198 of the leaf spring assembly 46. The spacer ring 232 has a generally T-shaped cross section profile so as to define a seating surface against which the body of the front drill housing 230 abuts. Drag ring 233 is located between spacer ring 232 and the flange 231 of front drill housing 230. While not illustrated, drag ring 233 is formed as a split ring.

A preload plunger 234 is slidably fitted in a bore 235 formed in the front drill housing 230. Preload plunger 234 is shaped so that the rear end thereof has an outwardly directed lip 236. The lip 236 of the preload plunger 234 is dimensioned to abut against a complementary step 237 formed in the bore of the front drill housing 230 that limits the forward movement of the preload plunger. Preload plunger 234 has an axially extending bore 238 designed to accommodate the shaft 32 of the cutting attachment 26. The exposed tip of the preload plunger is formed with an inwardly beveled surface 239 around bore 238.

A bearing assembly 240 is seated in a stepped space 241 (FIG. 10B) formed in head 194 of drill housing 44. Bearing assembly 240 provides a low friction interface between the shaft 32 of the cutting attachment 26 and the rear drill housing 44. A washer 243 rests on the top surface of bearing assembly 240. A spring 242 extends between washer 243 and a stepped surface inside the preload plunger 234 disposed around bore 238. Spring 242 urges preload plunger 234 in the forward direction.

Figure 12:
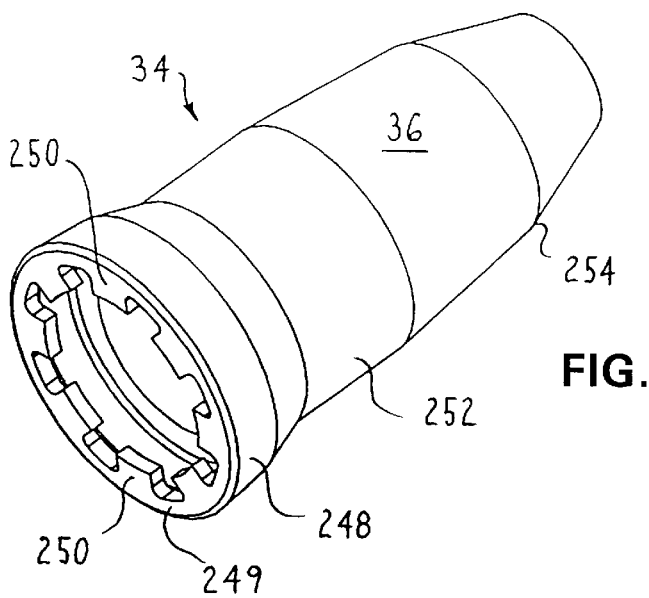
FIG. 12 is a detailed outside view of the attachment housing.
Figure 16:
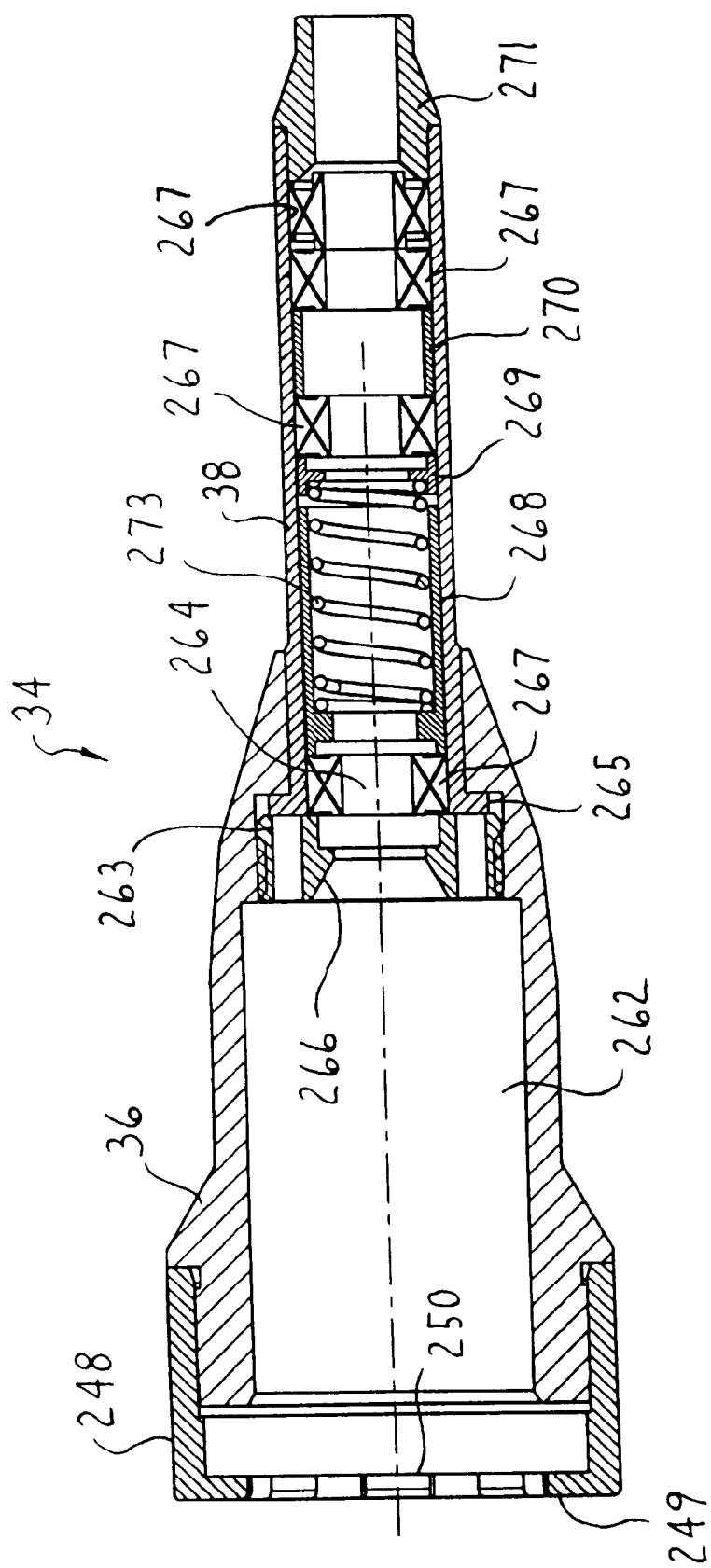
FIG. 16 is a cross sectional view of the attachment that is secured to the handpiece.

The attachment 34 in which a substantial length of the cutting accessory stem 32 is housed, is now described by reference to FIGS. 12 and 16. The attachment housing 36 is fitted over both drill housings 44 and 230. A retainer 248 is fitted over the rear circumferential surface of the attachment housing 36. Retainer 248 has an inwardly directed lip 249 that is spaced rearwardly away from the end of the attachment housing 36. Lip 249 is shaped to define the teeth 250 that fit into the complementary slots 182 formed in the rear drill housing 44.

Attachment housing 36 is formed to have a generally constant diameter base section 252. There is an inwardly tapered section 254 contiguous with the base section 252. The attachment housing 36 is further formed so as to have a constant diameter main space 262. The stem section 188 of the rear drill housing 44 is seated in space 262. Attachment housing 36 is further formed to have a reduced diameter space 263 inside tapered section 254. A bore 264 extends forward from space 263. Space 262, space 263 and bore 264 are coaxial with each other and extend through the attachment housing 36.

Sleeve 38 extends through bore 264. The sleeve 38 is formed with an outwardly extending lip 265 that abuts the surface of the attachment housing 36 that defines space 263. A bearing retainer ring 266 seated in space 263 holds sleeve 38 in position. A first bearing assembly 267 is fitted in the rear end of the sleeve 38 so as to abut bearing retainer ring 266. A tube-like bearing sleeve 268 is fitted within attachment sleeve 38 so as to abut bearing assembly 267. A bearing preload ring 269 is located above bearing sleeve 268. A second bearing assembly 267 is located adjacent preload ring 269. A preload sleeve 270 is located adjacent the second bearing assembly 267. Third and fourth bearing assemblies 267 are located in tandem adjacent preload sleeve 270. A nose cap 271 is fitted over the open end of sleeve 38 so as to abut the forwardmost, fourth bearing assembly 267. A spring 273 fitted in bearing sleeve 268 abuts the adjacent preload ring 269. Spring 273 imposes an axial force across the races of the forward bearing assembly 267 so as to reduce bearing chatter.

Figures 13A, 13B:
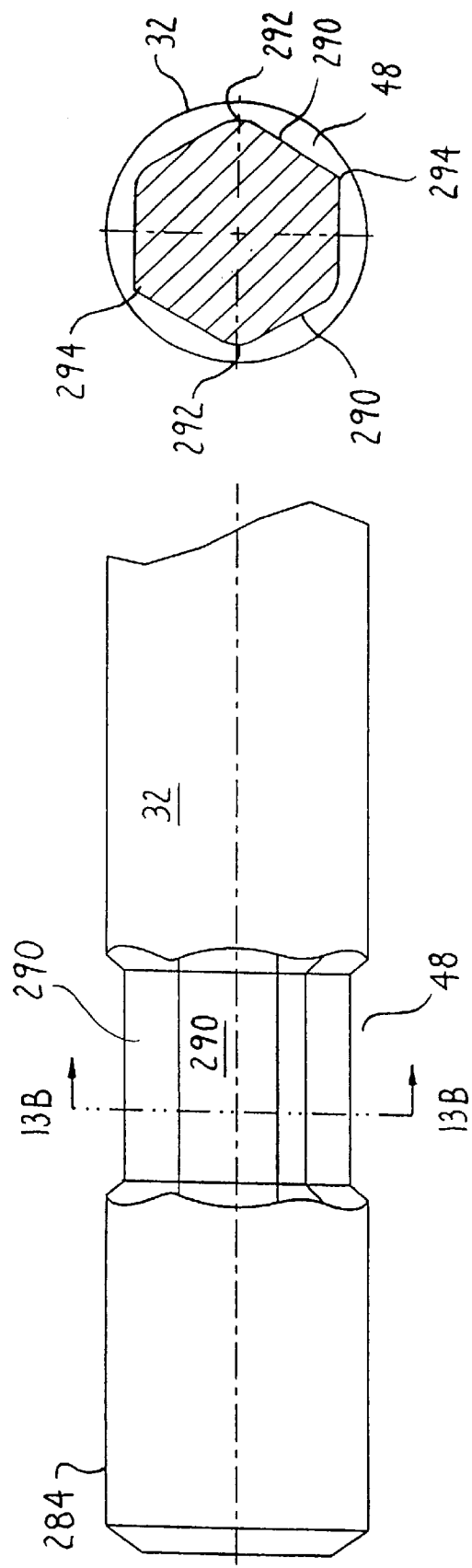
FIGS. 13A and 13B are, respectively, detailed and cross sectional views of the shaft of a surgical instrument of the surgical tool system of this invention.

The shaft 32 of the cutting accessory 26, as seen now by FIGS. 13A and 13B, has a butt end 284 which is seated in the shaft receiving space 106 of collet housing 80. Between the shaft butt end 284 and the rest of the shaft 32 is the shaft locking section 48 formed as a solid section integral with the rest of the shaft 32. Shaft lock ring 48 is shaped to have a number of flat faces 290 which are all recessed relative to the adjacent outer surfaces of the adjacent butt end 284 and the rest of the shaft 32. In the depicted version of the invention, shaft locking section 48 has six faces 290. Shaft lock ring 48 is further formed so as to have four rounded corners 292 between four pairs of adjacent faces 290. There are also two, diametrically opposed corners 294 with sharp, straight edges located between the remaining two pairs of abutting faces 290. The corners 294 with the straight edges are located further from the center axis of the shaft 32 than the corners 292 with the rounded edges.

Figure 14B:
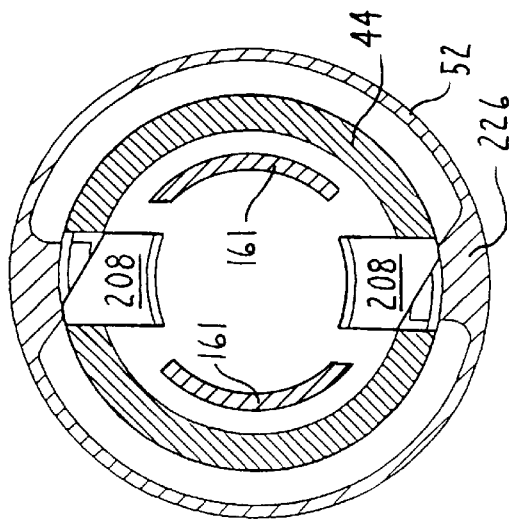
FIGS. 14A and 14B are, respectively cross sectional views illustrating the relationship of the actuating collar and locking leaf spring to the attachment housing when the actuating collar is in the locked and unlocked state.
Figure 14A:
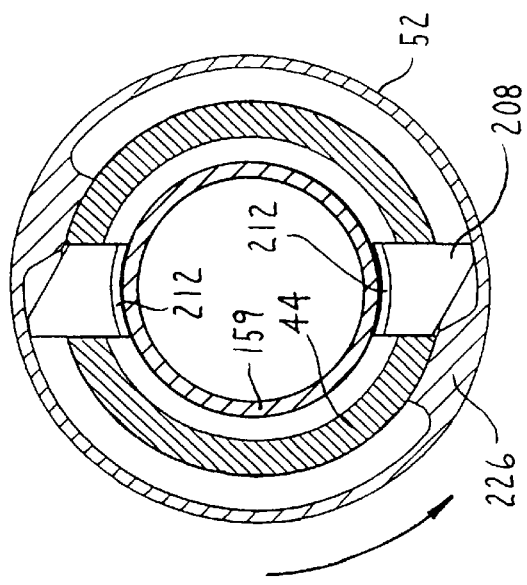

When the surgical tool system 20 of this invention is assembled for use, attachment 34 is seated over drill housings 44 and 230 and the cutting accessory shaft 32 is positioned so as to extend through the attachment and into the drill housings. As seen in FIG. 15A, the attachment 32 is positioned over the rear drill housing 44 so that the lock ring teeth 250 associated with the attachment housing 34 are fitted into the drill housing slots 182. When the attachment housing 34 is so positioned, the leaf spring locking tabs 204 are seated over two of the opposed lock ring teeth 250 so as to hold the attachment housing 34 in position. Moreover, when the attachment housing 34 is so positioned, the heels 212 of the leaf spring feet 208 are in close proximity to the adjacent outer surface of the intermediate section 159 of the collet actuator 154 as seen in FIG. 14A. The relative position of collet actuator 154 to feet 208 of the leaf spring assembly 46 prevents motor or cutting induced vibration of handpiece 22 from causing the feet to move inwardly and potentially release their hold on attachment 34.

The butt end 284 of the shaft 32 of the cutting accessory 26 is seated in the shaft receiving space 106 formed in the collet housing 80. Shaft 32 is locked in the housing by the action of the collet feet 128 bearing against three of the faces 290 formed in the shaft locking section 48. The collet ring 136 is latched in position against the collet legs 126 by the biasing force imposed by the spring 150. Consequently, the force of the edge surfaces 145 of the collet ring moving against the surfaces 135 of the collet feet produces the griping action of the collet feet 128. When the surgical tool system 20 is in the run state, ball bearings 160 are in their highest position along the actuating collar ball grooves 222. When ball bearings 160 are in this position, the ball bearings hold the collet actuator 154 in its most distal position relative to the rear drill housing 44. When the collet actuator 154 is in this position, the actuator web 165 is spaced above the adjacent collet ring upper web 146.

When the surgical tool system 20 is so assembled, the tool can be used in a conventional manner. Since the collet actuator web 165 is spaced from the adjacent collet ring upper web 146, the collet ring 136 as well as the associated elements attached thereto, the collet 50, collet housing 80, rotor shaft 60 and rotor 56 can then freely turn when energization voltages are applied to the windings 54 of the motor 24. Since the collet 50 firmly holds the shaft 32 in the collet housing 80, the motor-induced rotation of the collet housing 80 is thus transferred to the shaft. In this manner, the motive force generated by the motor 24 is thus transferred to the cutting accessory 26.

Figure 15B:
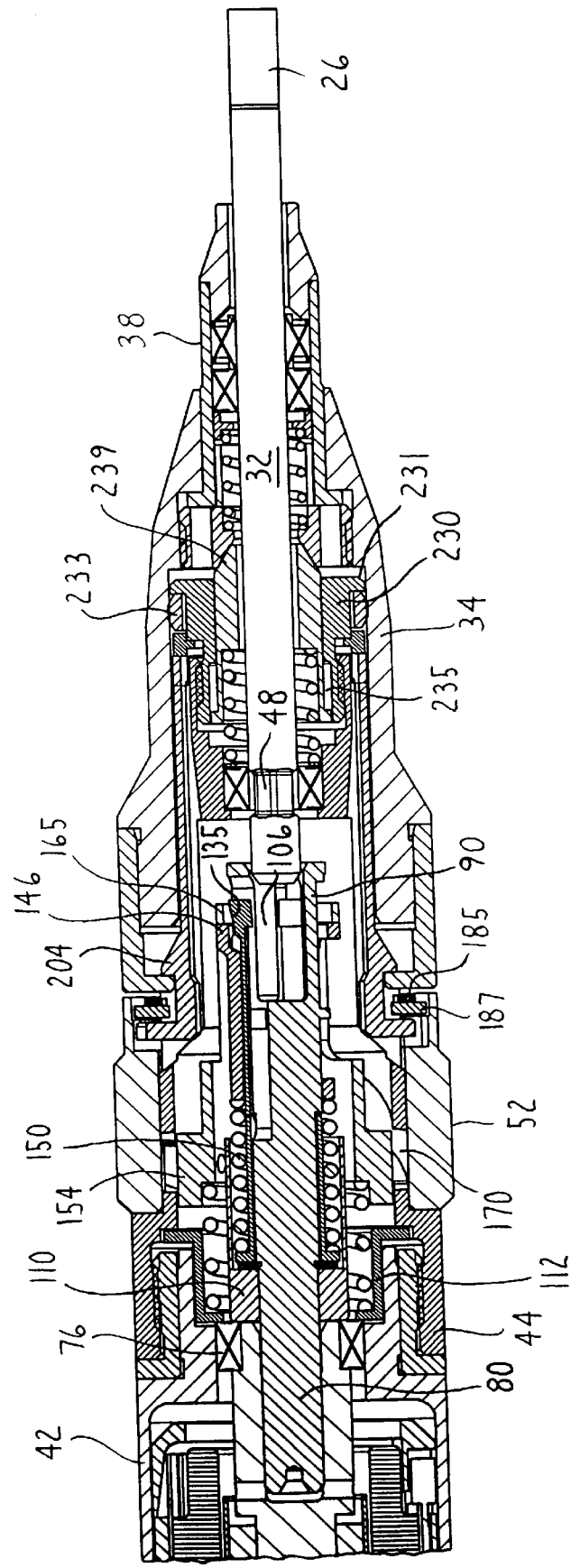

When the physician using the tool system 20 of this invention wishes to use it with a different cutting accessory 26, all that is necessary to do is to rotate the actuating collar 52. The actuating collar 52 causes the ball bearings 160 to move helical downwardly through the main sections 172 of the slots 170 formed in the rear drill housing 44. As represented by FIG. 15B, the downward movement of the ball bearings 160 forces the collet actuator 154 to undergo a similar rotating movement downward along the axis of the handpiece 22. As the ball bearings 160 are displaced through the slots 170, they will seat in the detents 174. The seating of ball bearings 160 in the detents 174 serves to lock the actuating collar 52 in place, in an accessory load state.

As the collet actuator 154 moves downwards, the actuator web 165 abuts against the collet ring upper web 146, best seen by reference to FIG. 15B. The continued movement of the collet actuator 154 forces the collet ring 136 downwardly so as to result in the compression of the spring 150 that abuts the ring 136. As the collet ring 136 moves downwards, away from the heels 130 of the collet feet 128, the collet legs 126 open up so that the collet feet move out of the shaft receiving space 106. The movement of the collet feet 128 out of the shaft receiving space 106 and away from the shaft butt end 284 frees the shaft 32 so that the cutting accessory 26 can be removed from handpiece 42.

Once the first cutting accessory 26 is removed from the handpiece 22, a second accessory can be loaded in place. Once the shaft 32 of the new accessory 26 is fitted in the handpiece 22, actuating collar 52 is manually rotated back to its initial, run, position. This movement causes the collet actuator 154 to be displaced upwardly so as to allow the collect ring 136 to return to its initial position. As the collet ring 136 returns to its normal position, the edges surfaces 145 of the legs 140 of the collet ring 136 force the feet 128 of the collet 50 inward towards the center of the shaft receiving space 106. The inward movement of the collet feet 128 forces them against the faces 290 of the shaft locking section 48 so as to lock the replacement cutting accessory 26 in position.

Figure 15C:
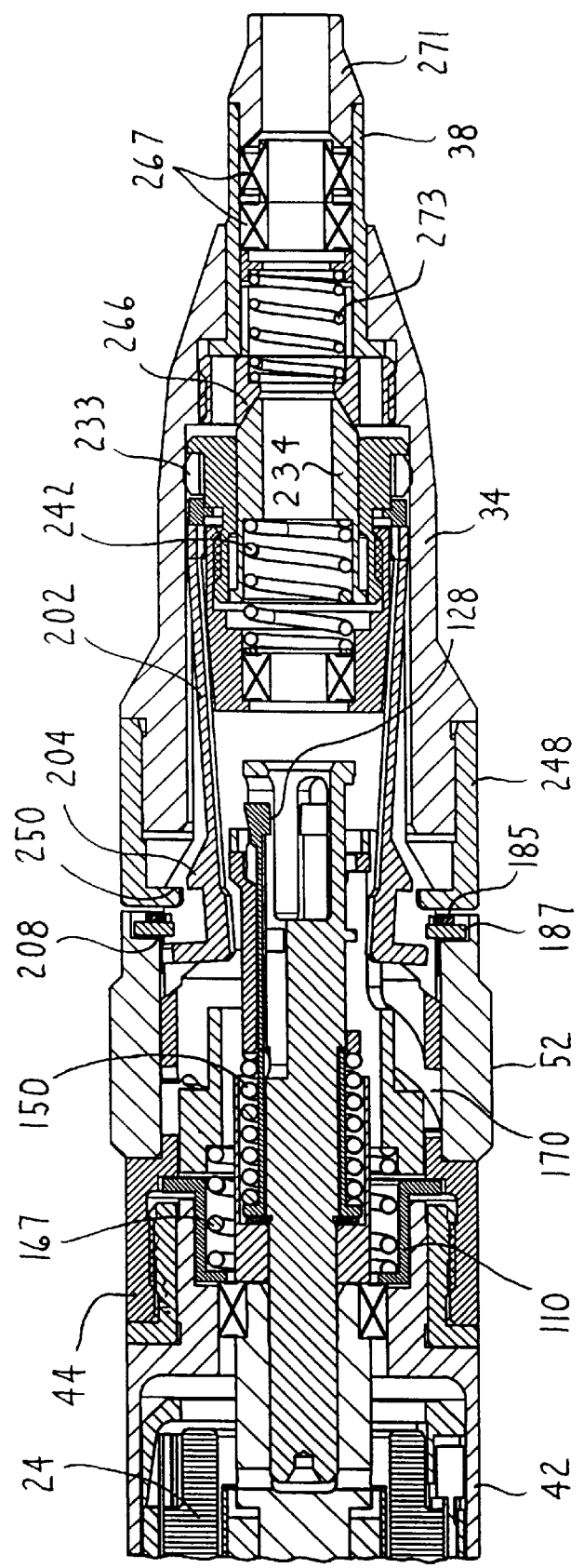

If the physician desires to replace the attachment 34 of the surgical tool system 20, actuating collar 52 is initially rotated in the manner required in order to unload the cutting accessory 26. The physician then continues to rotate actuating collar 52 so that the ball bearings 160 are displaced beyond the detents 174 and into the release sections 178 of slots 170. As a result of this further rotation of actuating collar 52, the tabs 226 associated with the collar stepped surface 224 are forced against the adjacent leaf spring feet 208 (FIG. 14B). Also, owing to the vertical displacement of the collet actuator 154, the actuator 154 is now spaced so that the leaf spring legs and feet 202 and 208, respectively are aligned with the interstitial spaces between the legs 161 of the actuator 154. Thus, the action of the tabs 226 moving against the leaf spring feet 208 forces the leaf spring legs 202 inwardly relative to the adjacent outer surface of the rear drill housing 4 as represented by FIG. 15C. The handpiece 22 is, at this time in the attachment release state. Once leaf spring legs 202 are disposed into the associated slots 192 formed in the rear drill housing 44, the attachment 34 is forced upwards a short distance by the action of the preload plunger 234 bearing against bearing retainer ring 266. The forward movement of the attachment housing 34 is, however, damped by the frictional contact imposed by the drag ring 233 against the adjacent surface of the attachment 34.

When the actuating collar 52 is in the attachment release state, the ball bearings 160 are in the base of the release sections 178 of slots 170. The release of the manual force on the actuating collar 52 allows the force imposed by springs 150 and 167 through the collet actuator 154 causes the actuating collar 52 to rotate backwards so as to take the leaf spring assembly 46 out of the attachment release state. More specifically, the actuating collar 52 will continue to rotate until the ball bearings 160 are seated in detents 174 so that the collet 50 remains in the accessory load state until otherwise actuated.

After the first attachment 34 is removed from the handpiece 22, the actuating collar 52 is returned to its original position. The replacement attachment 34 is then secured into position by simply snap locking it in place over the rear drill housing 44. A new cutting accessory 26 is then coupled into the handpiece 22. Once the new cutting accessory 26 is in place, the actuating collar 52 is manually actuated to return the handpiece from the accessory load state back to the tool run state.

The surgical tool system 20 of this invention thus provides a convenient system for using different cutting accessories 26 and different attachments 34 with a single handpiece 22. The cutting accessory 26 is coupled to the handpiece 22 for rotation with the rotor shaft 60 by collet 50. The attachment 34 is statically secured to the handpiece 22 by leaf spring 46. In the event there is a need to change the cutting accessory 26 or the attachment 34, all the surgical personnel have to do is rotate the actuating collar 56. No additional tools are required to change either the accessory or the attachment.

Furthermore, the handpiece 22 of this invention only has a single component, the actuating collar 52, that needs to be manipulated in order to change the cutting accessory 26 or the attachment 34. Since there is only one actuatable element attached to the handpiece 22, surgical personnel do not have to spend any time remembering which button or collar needs to be manipulated in order to switch the components used with the handpiece 22.

Moreover, still another feature of this invention is that once the actuating collar 52 is rotated into the accessory load state, the ball bearings 160 seat in the complementary detents 174 and are in held in this position by the force that springs 150 and 167 indirectly impose on collet actuator 154. Consequently, surgical personnel handling the handpiece 22 do not have to continue to hold the actuating collar 52 to ensure that the collet feet 128 remain in the unloaded state. By eliminating the need to have to hold the actuating collar 52 in the accessory load state, the surgical personnel can more closely focus on rapidly replacing the surgical cutting accessory 26. In a similar vein, all that is necessary to do fit a replacement attachment 34 to the handpiece is to snap fit the attachment in place.

Collectively, the elimination of multiple release actions, any need to hold the collet in the accessory loaded state or the leaf spring assembly 46 in the attachment release state serve to minimize the amount of time and effort surgical personnel need to take in order to change the tools and attachments with which this handpiece is used.

Still another feature of the system 20 of this invention is that when the actuating collar 52 is in any other position more than a few degrees off from the drill run state, the movement of the collar 52 forces the collet actuator 154 to abut against the collet ring 136. When the handpiece 22 is in this state, the force of the collet actuator 154 abutting the collet ring 136 prevents rotation of the collet ring and the components attached thereto. As a result of this breaking action, if the motor 24 is inadvertently actuated when the handpiece 22 is in this state, the collet rotor and all the elements attached thereto including the motor rotor 60 are prevented from moving. This serves as a fail safe to prevent the motor from inadvertently being used to supply rotational force to the accessory shaft when the accessory shaft is not properly locked in position.

The shape of the locking section 48 of the shaft 32 of the cutting accessory 26 also facilitates the rapid changing of the accessories. The reduced diameter rounded corners 292 of the lock ring 48 ensure that if the shaft 32 is not properly seated in the collet housing 80, the feet 128 of the collet 50 will upon closing, first strike the corners 294 with sharp edges. This will cause the shaft to rotate until each foot is in contact with a flat surface 290. Thus, this feature of the invention substantially reduces the possibility that the each of the collet feet 128 will not press against a complementary flat surface 290.

Figure 17:
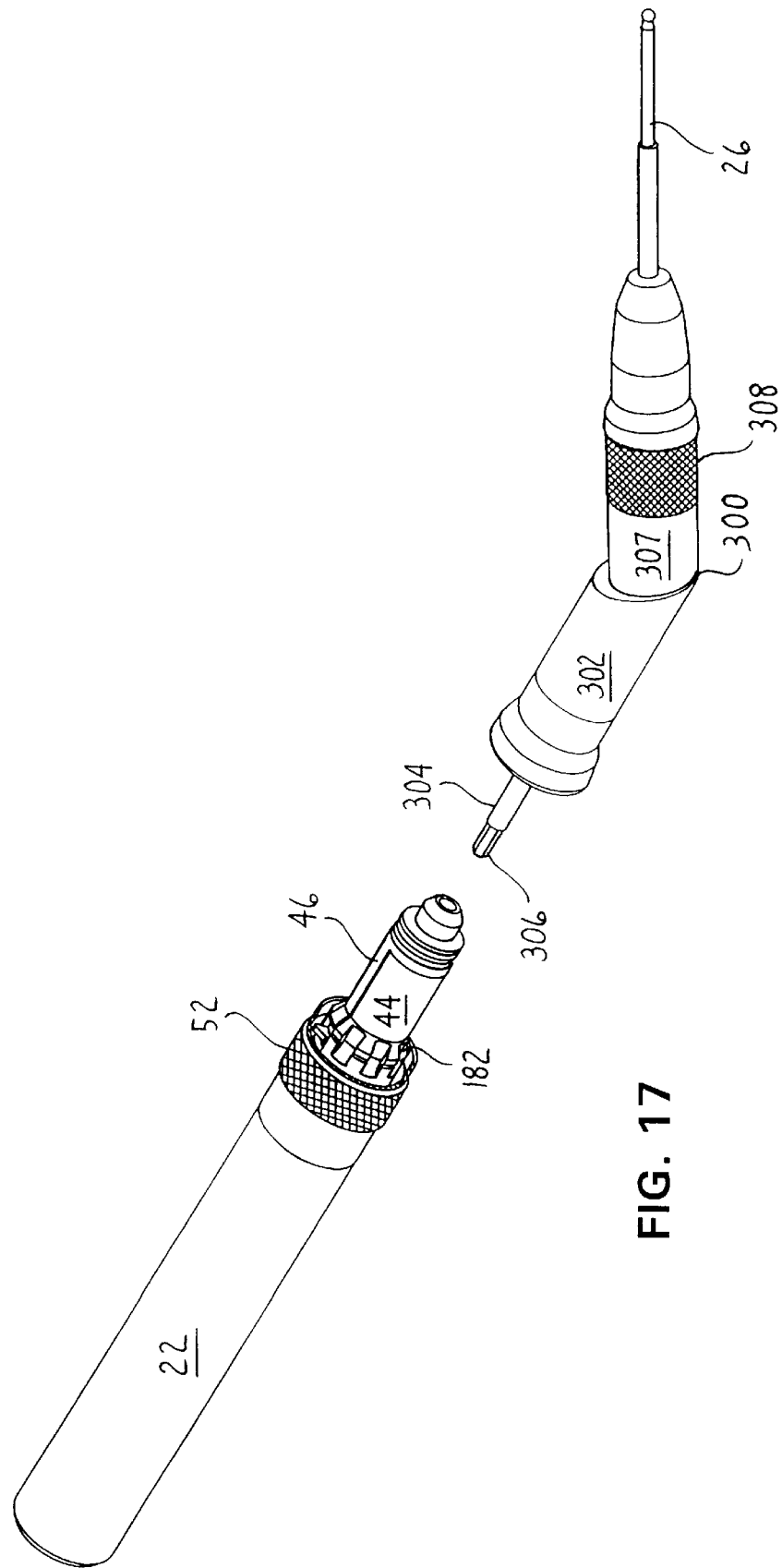
FIG. 17 is a perspective view illustrating how the surgical tool system of this invention can be used with an angled attachment.

FIG. 17 depicts an angled attachment 300 that can be used with the surgical tool system 20 of this invention. Attachment 300 has a base 302 with a retainer (not illustrated) designed to perform the function of previously described retainer 248. A drive shaft 304 is rotatably fitted to the base 302 and extends rearwardly therefrom. Drive shaft 304 is provided with a locking section 306 with surfaces similar to the surfaces similar to locking section 48 (FIG. 13B). In the illustrated version of the invention the flat faces that form locking section 306 extend to the butt end of shaft drive shaft 304. The drive shaft 304 is coupled into the collet housing 80 in a manner identical to that by which the shaft of a surgical tool is so secured.

A top section 307 integral with and angled from the base 302 extends forward the base. A coupling assembly similar to the described collet 50, collet housing 80, collet ring 136 and collet actuator 154 are disposed inside the top section 307 of the angled attachment 300 to facilitate the rotatable coupling of the stem 32 of a cutting accessory 26 thereto. An actuating collar 308 located around the outside of the top section is employed to move the coupling assembly between the loaded and unloaded states.

Also disposed within attachment 300 is a gear assembly for transferring the rotational moment of drive shaft 304 to the coupling assembly. Thus, the drive shaft 304, the gear assembly and the coupling assembly collectively transfer the rotational moment of the motor 24 of the handpiece 22 to the cutting accessory 26 attached to the angled attachment 300.

The foregoing description has been limited to a specific embodiment of this invention. It will be apparent, however, from the description of the invention that it can be practiced using components different from what has been described. For example, while in the described version of the invention, the motor 24 is an electrically actuated motor, in other versions of the invention the rotor shaft may either be driven pneumatically, hydraulically or mechanically. Furthermore, while in the described version of the invention a collet 50 with resilient feet 128 is employed to lock the shaft 32 of the cutting accessory 26 in place, in other versions of the invention, other locking members may be employed. For example, it may be possible to replace the collet with ball bearing or a set of spring loaded locking pins.

Also, the disclosed arrangement of the components of the components should likewise be recognized as exemplary. In some versions of the invention it may be possible, for example, to position the collet actuator so that it moves forward so as to cause the collet ring or similar component in a forward direction away from the collet 50.

Also, while only two attachments 34 and 300 for use as part of the surgical tool system 20 have been shown, others may, of course, be provided. For example, it may be desirable to provide an elongated attachment with a single axis centered on the axis of the handpiece 22. This would allow the cutting attachment to be positioned a relatively long distance away from the end of the handpiece 22. This attachment would have a drive shaft and a coupling assembly similar to the previously described angled attachment 300. Still other attachments could be provided with internal gear assemblies to convert the circular motion of the rotor shaft 60 into oscillating motion that would facilitate the use of handpiece with surgical cutting blades designed to move in sagittal pattern (in a plane parallel with the axis of the handpiece) or in an oscillatory motion (accessory movement in a plane angled from the axis of the handpiece). These attachments could then be used to attach saw blades to the handpiece 22 so that the saw blades could function as the cutting accessories 26. It should, of course, different angled attachments other than attachment 300 may be provided. For example, it may be possible to provide an angled attachment that facilitates the coupling of a cutting accessory to the handpiece at a right angle relative to the center axis of the handpiece 22.

Moreover, the locking section 48 of the shaft 32 of the cutting accessory 26 can have other shapes than what has been described. For example, it may be desirable to simply provide additional, relatively small facets instead of the described rounded corners. Also, it may be possible to shape the locking section so that four of the corners are spaced further from the center axis of the shaft than the other two corners. Moreover, while in the described version of the invention the locking section has six flat faces 290, other versions of the invention may have more or less faces and even an odd number of faces.

Therefore, it is the object of the appended claims to cover all such modifications and variations as come within the true spirit and scope of the invention.

What is claimed is:

1. An attachment for connection to a surgical handpiece, said attachment including:

an attachment housing, said attachment housing defining a center space for fitting said attachment housing over the surgical handpiece and said attachment housing having a base positioned to be located against the surgical handpiece and a plurality of teeth positioned to engage the surgical handpiece so as to hold said attachment housing static relative to said surgical handpiece; and a cylindrical shaft rotatably fitted to said attachment housing so as to extend through said center space of said attachment housing and into the handpiece, said shaft having a diameter and an axis and being further shaped to have a locking section integrally formed therewith, said lock ring being shaped to have a plurality of planar faces so as that said locking section has a polygonal cross section profile that has a diameter less than said diameter of said shaft wherein said faces forming said locking section meet at corners and said locking section is further shaped so that at least two corners are spaced a first distance from the axis of the shaft and at least one corner spaced a second distance from the axis of the shaft.

2. The attachment of claim 1, wherein said locking section of said shaft is further shaped so that at least two opposed corners thereof are shaped to define a straight edge between said faces forming said corners.

3. The attachment of claim 2, wherein said locking section has at least six said faces.

4. The attachment of claim 2, wherein said locking section is formed so as to have a single pair of opposed corners that define straight edges therebetween.

5. The attachment of claim 1, wherein said shaft is removably insertable into said attachment housing.

6. The attachment of claim 5, further including at least one bearing assembly disposed in said attachment housing so as to provide a rotating interface between said shaft and said attachment housing.

7. The attachment of claim 1, wherein: said attachment housing is formed with a first section containing said center space and a second section that is angled relative to said first section; said shaft is fixedly secured to said first section of said attachment housing; and a coupling assembling assembly is disposed in said second section of said attachment housing, said coupling assembly being configured to releasably secure a cutting accessory thereto, and said coupling assembly is connected to said shaft for rotating in response to rotational motion of said shaft.

8. The attachment of claim 1, wherein: said shaft is rotatably secured to said attachment housing; and a coupling assembly is disposed in said attachment housing for releasably receiving a cutting accessory, said coupling assembly being connected to said shaft for rotating in response to rotational motion of said shaft.

9. An attachment for connection to a surgical handpiece having a front end formed with slots, said attachment comprising: a housing having opposed front and rear ends, said housing having a center space extending forward from said rear end for fitting said housing over said surgical handpiece and a center bore that extends from said center space to said housing front end for accommodating a cutting accessory therein; and an inwardly directed lip integral with said housing located adjacent said rear end, said lip being formed with spaced-apart teeth that are inwardly directed towards the center space for engaging the slots in the surgical handpiece to prevent rotation of the attachment housing.

10. The attachment of claim 9, further including a retainer attached to said rear end of said housing that extends away from said housing wherein said lip is integrally formed with said retainer so as to be spaced from said housing.

11. The attachment of claim 9, further including at least one bearing assembly disposed in said housing so as to be located around said center bore for providing a rotating interface between a shaft in said center bore and said housing.

12. An attachment for coupling a cutting accessory to a surgical handpiece, the surgical handpiece having a motor; said attachment including:

an attachment housing have opposed front and rear ends, said attachment housing having a center space that extends forward from said rear end for positioning said attachment housing over the surgical handpiece and an inwardly directed lip located adjacent said rear end, said lip having teeth for engaging the surgical handpiece to prevent rotation of said attachment housing;

a drive shaft rotatably secured to said attachment housing that extends away from said rear end of said attachment housing for connection to the motor of the surgical handpiece; and a coupling assembly disposed in said front end of said attachment housing, said coupling assembly including:
  a collet housing coupled to said drive shaft to rotate with said drive shaft, said collet housing having an axially extending shaft bore for receiving a shaft of the cutting accessory, and said collet housing shaped to form at least one opening that extends into said shaft bore;
  a locking member position adjacent each said opening in said collet housing for selective positioning in said shaft bore of said collet housing so that when said locking member is positioned in said shaft bore of said collet housing, said locking member holds the shaft of the cutting accessory for rotation with said drive shaft and when said locking member is spaced from said shaft bore, the shaft of the cutting accessory is removable from said shaft bore of said collet housing;
  a lock ring disposed around said collet housing and displaceable along said collet housing from a first position wherein said lock ring abuts said locking member so as to latch said locking member into said shaft bore of said collet housing and a second position wherein said lock ring is spaced from said locking member;
  a biasing member that normally urges said lock ring into said lock ring first position;
  a lock ring actuator disposed around said lock ring for selectively abutting said lock ring to move said lock ring from said lock ring first position to said lock ring second position; and
  a displaceable actuating member that is fitted over said attachment housing and is coupled to said lock ring actuator, said actuating member being movable between a run position and an accessory load position, wherein when said actuating member is moved from said run position to said accessory load position, said actuating member causes said lock ring actuator to abut said lock ring so as to cause said lock ring to move to said lock ring second position and said actuating member remains in said accessory load position until displaced from said accessory load position.

13. The attachment of claim 12, wherein said actuating member is a collar rotatably fitted over said front end of said attachment housing.

14. The attachment of claim 12, wherein said attachment housing is formed from a first section containing said center space and from which said drive shaft extends and a second section that is angled from said first section wherein said coupling assembly is disposed in said second section.

15. The attachment of claim 12, wherein said drive shaft has a diameter and an elongated axis and is further shaped to have a locking section integrally formed therewith, said locking section being shaped to have a plurality of planar faces so as that said locking section has a polygonal cross section profile that has a diameter less than said diameter of said shaft wherein said faces forming said locking section meet at corners and said locking section is further shaped so that at least two corners are spaced a first distance from the axis of the shaft and at least one corner spaced a second distance from the axis of the shaft different from the first distance.

* * * * *

UNITED STATES PATENT AND TRADEMARK OFFICE
CERTIFICATE OF CORRECTION

PATENT NO. : 6,045,564
DATED : April 4, 2000
INVENTOR(S) : James G. Walen

Page 1 of 1

It is certified that error appears in the above-identified patent and that said Letters Patent is hereby corrected as shown below:

Column 15, line 3; change "said lock ring" to --- said locking section---.
Column 15, line 4; change "so as that" to --- so that---.
Column 16, line 67; change "so as that" to --- so that---.

Signed and Sealed this

Fifth Day of June, 2001

Attest:

NICHOLAS P. GODICI

*Attesting Officer*

*Acting Director of the United States Patent and Trademark Office*